(12) United States Patent
Pero et al.

(10) Patent No.: US 6,713,517 B1
(45) Date of Patent: *Mar. 30, 2004

(54) USE OF ARYL N-SUBSTITUTED CARBOXAMIDES DIRECTLY AND AS RADIO-AND CHEMOSENSITIZERS FOR KILLING TUMOR AND CANCER CELLS AND NOVEL COMPOUNDS FOR SUCH USE

(75) Inventors: Ronald W. Pero, Lund (SE); Anders Olsson, Dalby (SE); Tomas Ekberg, Lund (SE); Alan Schwartz, Piedmont, CA (US); David Chaplin, Aston Rowant (GB)

(73) Assignee: OXiGENE, Inc., Watertown, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 527 days.

(21) Appl. No.: 08/807,497

(22) Filed: Feb. 27, 1997

Related U.S. Application Data (60) Provisional application No. 60/013,072, filed on Mar. 8, 1996.

(51) Int. Cl.[7] ............................................. A01N 37/18
(52) U.S. Cl. ........................ 514/617; 514/619; 564/163
(58) Field of Search ................................. 514/619, 617; 564/163

(56) References Cited

U.S. PATENT DOCUMENTS

| | | | |
|---|---|---|---|
| 4,263,322 A | 4/1981 | van't Riet et al. | |
| 4,394,389 A | 7/1983 | van't Riet et al. | |
| 4,448,730 A | 5/1984 | van't Riet et al. | |
| 4,623,659 A | 11/1986 | van't Riet et al. | |
| 4,942,253 A | 7/1990 | van't Riet et al. | |
| 5,032,617 A | 7/1991 | Lee et al. | |
| 5,041,653 A | 8/1991 | Lee et al. | |
| 5,183,828 A | 2/1993 | van't Riet et al. | |
| 5,215,738 A | 6/1993 | Lee et al. | |
| 5,340,565 A | * 8/1994 | Pero ............................ | 424/10 |
| 5,350,770 A | 9/1994 | Elford et al. | |
| 5,366,996 A | 11/1994 | Elford et al. | |
| 5,561,129 A | 10/1996 | Pero | |
| 5,561,161 A | 10/1996 | Pero | |
| 6,100,299 A | * 8/2000 | Pero ........................... | 514/620 |

FOREIGN PATENT DOCUMENTS

| | | |
|---|---|---|
| EP | 0140958 | 12/1989 |
| EP | 0144396 | 1/1991 |
| EP | 0494623 | 7/1992 |
| WO | WO9312782 | 7/1993 |
| WO | 9324096 | 12/1993 |

OTHER PUBLICATIONS

Chemical Abstracts AN 1979:507575, Hanocq et al, Jan. 1979.*
Chemical Abstracts AN 1984:622098, Van Damme et al, Jan. 1984.*
Chemical Abstracts AN 1997:80406, Eisenhut et al, DE 19519508, Dec. 5, 1996.*
Merriam Webster's Collegiate Dictionary Tenth Edition, Springfield Mass.: Merriam Webster, Incorporated, p. 290, 1999.*
Ben Hur et al., Radiat. Res. 97:546 (1984).
Brown et al., Cancer Treatment Symposia 1, 85–101 (1984).
Charp et al., Biochim. Biophys. Acta 824:34 (1985).
Ganapthi et al., Biochem. Biophys. Res. Commun. 131:912–19 (1985).
George et al., Indian J. Expt. Biol. 22:305–07 (1984).
George et al., Int. J. Radiat. Biol. 49:783–98 (1986).
Horsman et al., Int. J. Radiat. Oncol. Biol. Phys. 12:1307–10, (1986).
Horsman et al., Radiat. Res. 118:139–50 (1989).
Horsman, Acta Oncologica 34:571–87 (1995).
Kennedy et al., Int. J. Radiat. Oncol. Biol. Phys. 12:1367–70 (1986).
Lazo et al., Cancer Res. 45:2103–09 (1985).
Lazo et al., Cancer Res. 46:2236–40 (1986).
Lybak et al., Carcinogenesis 12:1613–17 (1991).
Olsson et al., Carcinogenesis 16: 1029–35 (1995).
Pu et al., Oncology 9(8) :707–21 (1995).
Rosenthal et al., Yale J. Biol. Med. 61:39–49 (1988).
Schreiber et al., Cancer Res. 52: 3262–66 (1992).
Thompson, Science 267:1456–62 (1995).

* cited by examiner

*Primary Examiner*—Padmashri Ponnaluri
(74) *Attorney, Agent, or Firm*—Cooper & Dunham LLP (57) ABSTRACT

Methods of killing tumor or cancer cells in human patients using an aryl N-substituted carboxamide having one or more aryl halo or one or more aromatic nitrogens, and/or acid addition salts thereof. The carboxamide may be an N-substituted nicotinamide or an N-substituted benzamide having such features, and may be used directly as a chemotherapeutic agent, or as a sensitizer for radiation or other chemotherapeutic agents. New compositions for such use include N-(2-diethylamino-ethyl)-4-amino-3-chlorobenzamide, N-(2-diethylamino-ethyl) nicotinamide, and their acid addition salts, e.g. hydrochlorides.

3 Claims, 6 Drawing Sheets

USE OF ARYL N-SUBSTITUTED CARBOXAMIDES DIRECTLY AND AS RADIO-AND CHEMOSENSITIZERS FOR KILLING TUMOR AND CANCER CELLS AND NOVEL COMPOUNDS FOR SUCH USE

CROSS-REFERENCE TO RELATED APPLICATION

This application is a continuation of applicants' U.S. provisional patent application No. 60/013,072, filed Mar. 8, 1996.

BACKGROUND OF THE INVENTION

This invention relates to methods of inhibiting or killing tumor and cancer cells in human patients using aryl N-substituted carboxamides such as N-substituted benzamides and nicotinamides as direct chemotherapeutic agents or as sensitizers for radiation and/or other chemotherapeutic agents, and to novel aryl N-substituted benzamides and nicotinamides for such use.

A variety of chemical structures including the nitroimidazoles, phenothiazines, butyrophenones, halopyrimidines, benzamides and nicotinamides are known to possess radio- and chemosensitizing properties (Horsman, M. R. et al., Acta Oncologica 34:571, 1995; Brown, J. M. et al., Cancer Treatment Symposia 1, 85–101, 1984; Pu, A. T. et al., Oncology 9(8):707–21, 1995; George, K. C. and Singh, B. B., Indian J. Expt. Biol. 22:305–07, 1984; Kennedy, K. A. et al., Int. J. Radiat. Oncol. Biol. Phys. 12:1367–70, 1986; U.S. Pat. No. 5,340,565; Charp, P. A. and Regan, J. D., Biochim. Biophys. Acta 824:34–39, 1985, Ganapthi, R. et al., Biochem. Biophys. Res. Commun. 131:912–19, 1985; Lazo, J. S. et al., Cancer Res. 45:2103–09, 1985; Lazo, J. S. et al., Cancer Res. 46:2236–40, 1986). Common chemical structural features linking these diverse agents as radio- and chemosensitizers are not known in the prior art. U.S. Pat. Nos. 5,340,565, 5,215,738, 5,032,617 and 5,041,653 teach that benzamides and nicotinamides can radio- and chemosensitize by several mechanisms of action including by inhibiting DNA repair, by directly damaging DNA and by increasing tumor blood flow thus decreasing hypoxic resistance to tumor cell killing. The chemical features previously identified giving these classes of drugs radio- and chemosensitizing properties were di, mono- or un-N-substituted (—$CONH_2$) or (—$CSNH_2$) substitutions of the pyridine and benzene rings along with other aryl substitutions in structures I, II and III described below.

Structure I (from U.S. Pat. No. 5,340,565) has the formula (I)

wherein
X is any compatible aliphatic or aryl mono (—NHX) or di-substitutions (—$NX_2$); and
Y can be from 0 to 5 substitutions of a compatible chemical structure, for example (but not limited to) a group consisting of: H, OR, SR or NHR in which R is H, hydrocarbyl (1–6 C) including cyclic and unsaturated hydrocarbyl, optionally substituted with 1 or 2 substituents selected from the group consisting of halo, hydroxy, epoxy, alkoxy, alkylthio, amino including morpholino, acyloxy and acylamido and their thio analogs, alkylsulfonyl or alkylphosphonyl, carboxy or alkoxycarbonyl, or carbamyl or alkylcarbamyl, and in which R can optionally be interrupted by a single ether (—O—) linkage; or Y is O(CO)R, NH(CO)R, O(SO)R, or O(POR)R in which R is as above defined.

Structure II (from U.S. Pat. No. 5,215,738) has the formula (II)

wherein
X is O or S; and
Z is H, OR, SR or NHR in which R is H, hydrocarbyl (1–6 C) including cyclic and unsaturated hydrocarbyl, optionally substituted with 1 or 2 substituents selected from the group consisting of halo, hydroxy, epoxy, alkoxy, alkylthio, amino including morpholino, acyloxy and acylamido and their thio analogs, alkylsulfonyl or alkylphosphonyl, carboxy or alkoxycarbonyl, or carbamyl or alkylcarbamyl, and in which R can optionally be interrupted by a single ether (—O—) linkage; or Z is O(CO) R, NH(CO)R, O(SO) R, or O(POR) R in which R is as above defined.

Structure III (from U.S. Pat. No. 5,041,653) has the formula (III)

wherein
x is O or S;
Y is H, Me, OMe, OEt acetoxy or acetamido; and
Z is OR or NHR in which R is H, straight chain alkyl (1–6 C) optionally substituted with 1 or 2 substituents selected from the group consisting of halo, hydroxy, epoxy, alkoxy, amino, acyloxy and acylamido, and in which R can optionally be interrupted by a single ether (—O—) linkage; or O(CO)R or NH(CO)R in which R is as above defined.

In addition, prior art teaches that some analogs of the benzamides (Lybak, S. and Pero, R. W., Carcinogenesis 12:1613–17, 1991; Olsson, A. et al., Carcinogenesis 16:1029–35, 1995; George, A. M. et al., Int. J. Radiat. Biol. 49:783–98, 1986; Horsman et al., Int. J. Radiat. Oncol. Biol. Phys. 12:1307–10, 1986), nicotinamides (Horsman, M. R. et al., Radiat. Res. 118:139–50, 1989; Ben Hur, E. et al., Radiat. Res. 97:546, 1984; Horsman, M. R., Acta Oncologica 34:571, 1995), phenothiazines (Rosenthal, S. A. and Hart, W. N., Yale J. Biol. Med. 61:39–49, 1988), butyrophenones (U.S. Pat. No. 5,340,565) and halopyrimidines (Pu, A. T. et al., Oncology 9(8):707–21, 1995) can either directly by reacting with DNA, or directly by reacting with some chemical intermediate that in turn is converted to a DNA reactive intermediate, or indirectly by causing an increase in oxygen uptake by tumors which in turn can form DNA binding radicals, or indirectly by inhibiting DNA repair, cause DNA and other cell constituents to become damaged resulting in antitumor or radio- and chemosensitization. However, there is no prior knowledge in the literature that there are common chemical structural features which can give this diverse group of agents properties of antitumor or radio- and chemosensitization by a variety of mechanisms that amplify the levels of cellular DNA damage.

Among the specific compounds thus considered in the prior art are nicotinamide (hereinafter sometimes referred to as NAM), 4-amino-5-chloro-N-(2-diethylamino-ethyl)-2-methoxybenzamide (hereinafter sometimes referred to as metoclopramide or MCA), and their acid addition salts, e.g. metoclopramide hydrochloride (metoclopramide HCl).

SUMMARY OF THE INVENTION

The present invention, in a first aspect, broadly contemplates the provision of a method of inhibiting or killing tumor or cancer cells in a human patient, consisting essentially of treating the patient with a composition selected from the group consisting of aryl N-substituted carboxamides having one or more aryl halo or one or, more aromatic nitrogens, acid addition salts of these carboxamides, and mixtures thereof. In this method, the defined carboxamides act directly as chemotherapeutic agents, not merely as sensitizers for radiation and other chemotherapeutic agents. The term "consisting essentially," as used in the definition of the above-described method, excludes the use or presence of radiation or chemotherapeutic agents (other than the stated carboxamides and/or acid addition salts thereof) in the practice of the method.

The invention in a second aspect contemplates the provision of a method of inhibiting or killing tumor or cancer cells in a human patient, consisting essentially of treating the patient with radiation or a chemotherapeutic agent together with a composition selected from the group consisting of N-substituted nicotinamides, N-(2-diethylamino-ethyl)-4-amino-3-chlorobenzamide (hereinafter sometimes referred to as 3-chloro-procainamide or 3-CPA), their acid addition salts, and mixtures thereof, in an amount effective to enhance the cytotoxicity of the radiation or chemotherapeutic agent employed. The selected composition, in the latter method, acts as a sensitizer for the radiation or chemotherapeutic agent. The compositions used as such sensitizers, in accordance with the invention in this aspect, are novel in themselves or have at least not heretofore been recognized as capable of acting as sensitizers in radiation or chemotherapeutic treatments. They are within the broadly defined class of aryl N-substituted carboxamides having one or more aryl halo or one or more aromatic nitrogens.

In further important specific aspects, the invention contemplates the provision of certain novel compositions within the last-mentioned class and suitable for use in the practice of one or more of the above-stated methods of the invention; and the use of such compositions in the same methods. These compositions are the compounds N-(2-diethylamino-ethyl)nicotinamide (which is an N-substituted nicotinamide, and is hereinafter sometimes referred to as N-NAM), N-(2-diethylamino-ethyl)-4-amino-3-chlorobenzamide (i.e., 3-chloro-prcainamide, mentioned above), their acid addition salts, and mixtures thereof. Preferred acid addition salts are the hydrochlorides, viz., N-(2-diethylaminoethyl) nicotinamide HCl and 3-chloro-procainamide HCl.

Stated broadly, the invention in significant aspects is based on the identification of chemical features that impart properties of radio- and chemosensitization to some members of the group of agents discussed in the above-cited prior art, and embraces the discovery that agents having such properties include a new class of drugs called the N-substituted nicotinamides (e.g. N-NAM).

None of the prior art discussed above teaches the chemical features important to the present invention. For example, this invention embraces the discovery that the presence of an aryl constituent containing one or more halo substitutions (e.g. a halogenated benzamide), or an aromatic nitrogen (e.g. nicotinamide), or an equivalently appropriate reactive aromatic substitution (e.g. an aromatic sulfur (—S—) or oxygen (—O—)) needs to be combined with an N-substitution of the amide group of an existing carboxamide group (e.g. diethylaminoethyl side chain group) to give the resulting molecules the properties of inhibition of DNA repair, potentiation of DNA damage and a sensitized cytotoxicity.

These features may be represented by formula (A)

(A)

wherein

W is O or S;

Q is MHX or MX$_2$ where M is N, O or S and X is any compatible aliphatic or aryl substitution;

Y can be from 0 to 5 substitutions of a chemical structure, for example, but not limited to a group consisting of: H, OR, SR or NHR in which R is H, hydrocarbyl (1–6 C) including cyclic and unsaturated hydrocarbyl, optionally substituted with 1 or 2 substituents selected from the group consisting of halo, hydroxy, epoxy, alkoxy, alkylthio, amino including morpholino, acyloxy and acylamido and their thio analogs, alkylsulfonyl or alkylphosphonyl, carboxy or alkoxycarbonyl, or carbamyl or alkylcarbamyl, and in which R can optionally be interrupted by a single ether (—O—) linkage; or Y is O(CO)R, NH(CO)R, O(SO)R, or O(POR)R in which R is as above defined; and Z is one or more aromatic halo substitutions or one or more aromatic nitrogens or appropriately equivalent reactive aromatic substitutions such as a ring sulfur (i.e., —S—) or oxygen (—O—).

These structural requirements can be satisfied by benzamide and nicotinamide analogs as well as condensed aromatic ring systems such as suggested by but not limited to: quinolines, anthracenes, anthraquinones, quinones, phenothiazines, naphthalenes, and butyrophenones that contain a substitutable nitrogen (e.g. carboxamide) and at least one aromatic halo or aromatic nitrogen substitution.

Theoretically the discoveries embraced by the invention also teach that the N-substituted carboxamide structural requirement for antitumor or radio- and chemosensitizing properties could be replaced by an aryl carbonyl containing ester (aryl-COO—R, aryl-COS—R or aryl-COP—R) where R is equal to any substitutable aliphatic or aromatic group (e.g. a diethylaminoethyl side chain).

The invention in important respects, therefore, relates to the discovery of the chemical structural features that are important to give drugs antitumor or radio- and chemosensitizing properties, of potentiation of DNA damage resulting in tumor cytotoxicity. In its broadest sense, the essential common chemical features are an aryl N-substituted carboxamide and either at least one aromatic halo or aromatic nitrogen. The N-substituted benzamide analog, procainamide, will be shown here to be inactive because it did not contain an aromatic halo substitution along with the presence of an aryl N-substituted carboxamide (e.g. the diethylaminoethyl side chain present in metoclopramide or 3-chloro-procainamide). Moreover, metoclopramide and 3-chloroprocainamide but not procainamide could be shown to react with radiation which is a potential radiosensitizing event. These data are shown to be paralleled by in vitro cytotoxicity data that established metoclopramide and 3-chloro-procainamide, but again not procainamide, as having the properties to sensitize apoptotic cell killing by radiation. Together the data presented here indicate that both halo aromatic substitutions as well as N-substituted benzamides are necessary to give antitumor or radio- and chemosensitizing properties.

In another aspect this invention relates to the presence of an aromatic nitrogen substitution together with the presence of an aryl carboxamide to give antitumor or radio- and chemosensitizing properties. Such drugs are represented by the N-substituted nicotinamides or pyrazinamides for which N-(2-diethylamino-ethyl)nicotinamide is an example. In addition, it is now found that although N-(2-diethylamino-ethyl)nicotinamide, and to a much lesser degree nicotinamide, possess the potential radio-sensitizing property of reacting with radiation as a mechanism of initiating oxidative stress and increasing the potential for DNA damage induction, it is only N-(2-diethylamino-ethyl) nicotinamide and not nicotinamide, that can enhance apoptotic cell killing by radiation. It is hypothesized that an N-substitution of the carboxamide group of nicotinamide blocks the metabolic conversion of the nicotinamide moiety to NAD, and thus allows the chemical reactivity of the aromatic nitrogen with radiation to produce stress-induced cellular damage, and consequently, potentiates apoptotic cell killing by radiation plus the drug. It is clear then that N-substitutions of the carboxamide of nicotinamide permit the aromatic nitrogen to react with radiation or other radical generating systems to initiate an oxidative stressing cascade, instead of allowing the normal aromatic nitrogen cellular reaction of nicotinamide with the ribose moiety of adenine dinucleotide to form the energy source, NAD. These properties of N-substituted nicotinamides are novel and have never been heretofore described. They constitute a new class of agents with a high potential to possess antitumor or radio- and chemosensitizing properties.

Moreover, it should be noted that because both N-substituted benzamides (as shown in U.S. Pat. No. 5,340,565) and N-substituted nicotinamides (as now discovered, as an aspect of the present invention) possess antitumor or radio- and chemosensitizing properties, there is a great likelihood that other aromatic condensed ring systems can be identified that contain similar prerequisite structural moieties including, but not limited to a N-substituted aryl carboxamide giving such agents antitumor or radio- and chemosensitizing properties.

Additionally it may be noted that certain components of formula (III) above, wherein Z is in the 3-position, and wherein Z is OR or NHR in which R is substituted or interrupted with —O—, or Z is O(CO)R or NH(CO)R in which R is substituted or interrupted with —O—, are novel.

Further features and advantages of the invention will be apparent from the detailed description hereinbelow set forth, together with the accompanying drawings.

BRIEF DESCRIPTION OF THE DRAWINGS

FIG. 6B shows the average±S.D. and (*) indicates a significant difference versus control, t-test p<0.01 and (**) a significant difference versus radiation only, p<0.02.

DETAILED DESCRIPTION

The methods and compositions of the invention will be described and exemplified by the illustrative procedures and experimental data now to be set forth.

In these procedures, the sources of commercially available drugs and chemicals were as follows:

Nicotinamide, procainamide (4-amino-N-(2-diethylamino-ethyl)benzamide), and all organic solvents and general chemicals were supplied as analytical grade products from Sigma Chemical Company. Metoclopramide HCl (4-amino-5-chloro-N-(2-diethylamino-ethyl)-2-methoxybenzamide hydrochloride) was supplied as the formulated products identified by trademarks "Sensamide" and "Neu-Sensamide" by Oxigene, Inc. The novel compounds 3-chloro-procainamide (N-(2-diethylamino-ethyl)-4-amino-3-chlorobenzamide) and N-(2-diethylamino-ethyl) nicotinamide, and their respective hydrochlorides, were newly synthesized by oxigene by the following procedures:

Novel Synthesis of 3-Chloro-procainamide Hydrochloride [N-(2-Diethylamino-ethyl)-4-amino-3-chlorobenzamide Hydrochloride] (1a)

3-Chloroprocainamide Hydrochloride (1a)

Ethyl 4-amino-3-chlorobenzoate (2). Ethyl p-aminobenzoate, 49.50 g (0.30 moles) was dissolved in 500 ml of acetonitrile (CH₃CH) and heated to reflux. When the mixture became homogeneous, 42.0 g (0.315 moles) of N-chlorosuccinimide was added in several portions over one hour and the mixture was stirred at reflux overnight. By TLC (Hexane: EtOAc, 3:1), the mixture contained no starting material but only the desired product (Rf=0.55) and a minor impurity, which was probably dichlorinated material (Rf=0.65). The mixture was concentrated on a rotary evaporator and the residue was redissolved in 250 mL of dichloromethane (CH₂Cl₂) and washed twice with 100 mL of 5% sodium hydroxide (NaOH). The organic layer was dried over anhydrous potassium carbonate (K₂CO₃) and concentrated on a rotary evaporator to yield 62.0 g of a reddish brown solid. The solid was recrystallized from 1.25 L of boiling hexane to give 52 g of a brown solid. The solid was recrystallized twice more from 1 L of boiling hexane to give 45.5 g (76%) of tan solid ethyl 4-amino-3-chlorobenzoate (2), mp 82–83° C. and homogeneous by TLC. Additional material, 9.6 g (16%) of like quality, was obtained by repeated recrystallization from hexane. The total yield of pure ethyl 4-amino-3-chlorobenzoate (2) was 92%. 1H NMR (CDCl₃) d 7.97–7.96 (t, 1H, J=0.7 Hz, ArH), 7.80–7.75 (dt, 1H, J=0.7 Hz, ArH), 6.77–6.73 (dd, 1H, J=0.5 Hz, ArH), 4.40–4.29 (q, 2H, J=2.8 Hz, OCH₂), 1.41–1.34 (t, J=2.8 Hz, 2H, OCH₂CH₃). IR (KBr) cm⁻¹, 3500, 3370 (NH₂, m), 1695, (C=O, s) 1630. MS (El) m/e 199 (M+), 201 (M+2), Anal. Calc'd for C₉H₁₀NO₂. Cl: C, 54.15; H, 5.05: N, 7.02. Fd. C, 54.14; H, 5.17, N, 6.93.
The formula is:

Ethyl 4-Amino-3-chlorobenzoate (2)

4-Amino-3-chlorobenzoic acid (3). The benzoate ester (2), 45.5 g (0.23 moles), was dissolved in 250 mL of hot MeOH and then 230 mL of 3N NaOH (3 equivalents, 0.69 moles) was added. The mixture was stirred at reflux for 5 hours. The solution was concentrated on a rotary evaporator at 80° C. to remove the MeOH and then the mixture was acidified to pH 2 with 3N HCl. The precipitated solids were filtered on a sintered glass funnel and washed with water. The product was homogeneous by TLC (Hexane: EtOAc, 4:1, Rf=0.1) and therefore was not further purified. The white solid was dried at 70° C. in a vacuum oven to give 38.1 (97%) of 4-amino-3 chlorobenzoic acid (3), mp 225–226° C. 1H NMR (DMSO d₆) d 7.70 (d, 1H, J=0.9 Hz, ArH), 7.61–7.56 (dd, 1H, J=0.7 Hz, ArH), 6.78 (d, 1H, J=3.4 Hz, ArH), 6.15 (bs, 2H, NH₂). IR (KBr) cm⁻¹, 3515, 3410 (NH₂, m), 1675, (C=O, s) 1640. MS(El) m/e 171 (M+), 173 (M+2). Anal. Calc'd for C₇H₆NO₂Cl: C, 49.00; H, 3.62; N, 8.16. Fd. C, 49.22; H, 3.71, N, 7.9. The formula is:

4-Amino-3-chlorobenzoic Acid (3)

Figure 5:
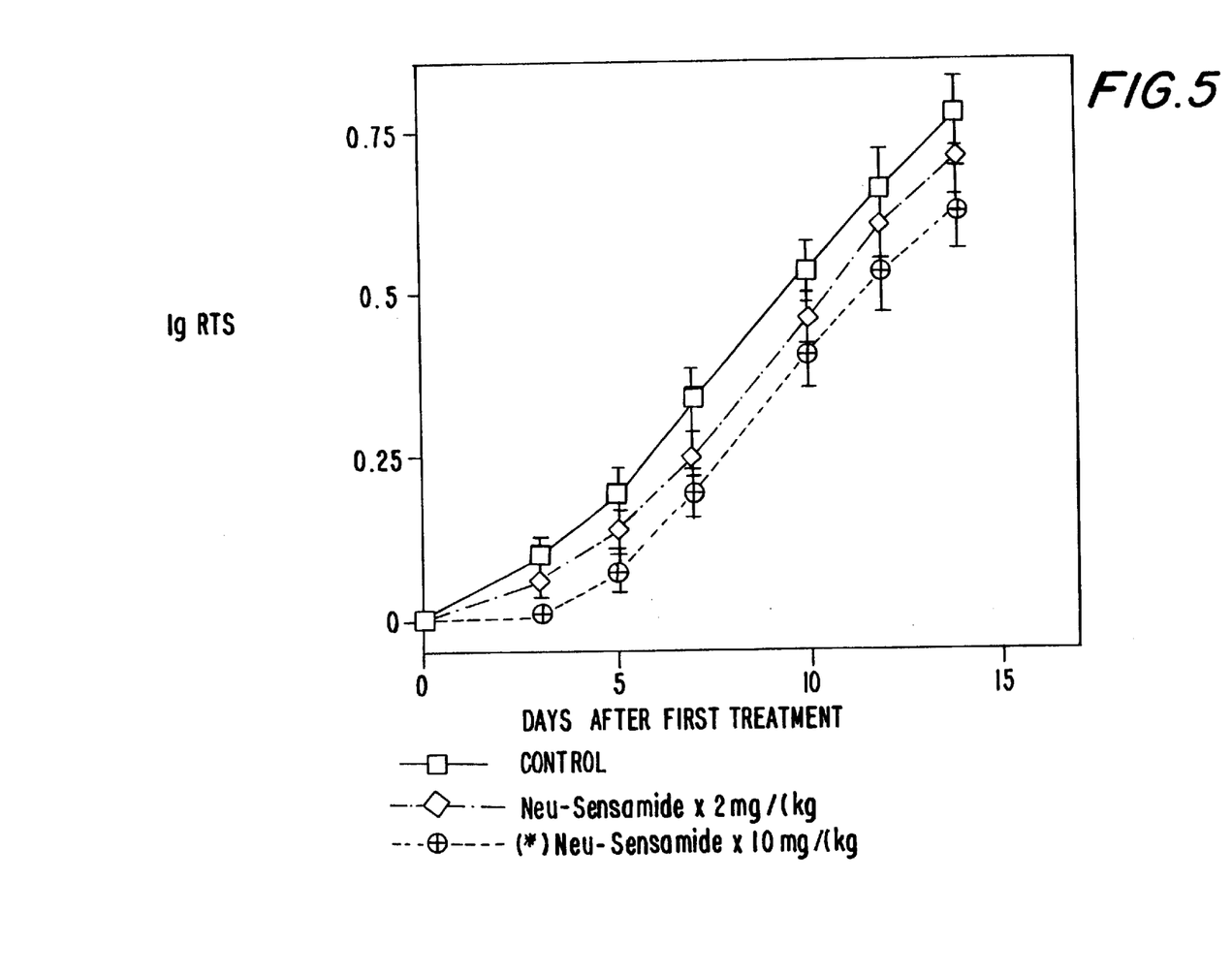
FIG. 5 is a graph of growth curves of a human lung adenocarcinoma (H2981) xenografted into scid mice treated with NeuSensamide™ (a conformationally altered formulation of 4-amino-5-chloro-N-(2-diethylamino-ethyl)-2-methoxybenzamide or metoclopramide) at repeated doses of 2 and 10 mg/kg (i.m.) 3 times per week (Monday, Wednesday, Friday), wherein each data point represents the mean±S.E.M. of 16 to 30 animals, (*) indicates a statistically significant difference (AUC, t-test, p<0.03) between the control group and the treated group at 10 mg/kg repeated dose.

3-chloro-procainamide, free base, [N-(2-diethylamino-ethyl)-4-amino-3-chlorobenzamide, free base] (1b). The acid (2), 10 g (0.058 moles) was dissolved in 800 mL of anhydrous THF. Carbonyl diimidazole, 11.1 g (0.067 moles), was added in one portion and the mixture was warmed to 35° C. CO₂ began to slowly evolve and then increased rapidly. After one hour, all evolution of gas ceased and the mixture was warmed to 45° C. for fifteen minutes to insure that all of the acid had reacted. N,N'-diethylenediamine, 7.5 g (0.65 moles) was added dropwise over five minutes and then the reaction mixture was warmed to 55° C. After 30 minutes, a TLC of the mixture (CH₂Cl₂:MeOH, 3:1) showed that the reaction was complete, producing the desired product (Rf 0.4) along with a minor nonpolar impurity (Rf 0.8) and polar impurities (Rf 0.1). The TCL did not change after stirring overnight at 55° C. The solvent was removed on a rotary evaporator at 50° C. and then 100 mL of water was added to destroy any unreacted carbonyl diimidazole, producing a biphasic mixture. The free base was extracted into CH₂Cl₂ (3×100 mL), and dried over anhydrous K₂CO₃, and evaporated to give 20 g (>100%) of a brown oil. Attempts to prepare a crystalline salt (sulfate, succinate, tosylate, and adipate) failed. Simple chromatography on 25 g of silica, eluting with hexane:EtOAc (2:1) gave 14.3 g (91%) of 1b as clear tan oil, homogeneous by TLC. The structure of the free base (1b) is shown in FIG. 5. 1H NMR (CDCL₃) d 7.75 (d, J=0.8 Hz, 1H, ArH), 7.52–7.48 (dd, J=0.8 Hz, 1H, ArH), 6.84 (bs, 1H, NH), 6.77–6.74 (d, J=2.8 Hz, 1H, ArH), 3.49–3.43 (q, 2H, J=1.8 Hz, CH₂NHCO), 2.66–2.54 (m, 6H, (CH₂)₃N, 1.07–1.02 (t, J=2.4 Hz, 6H, N(CH₂CH₃)₂). IR (KBr) cm⁻¹, 3475, 3320 (NH₂, m), 1620, 1600 (C=O, s). MS (El) m/e 269 (M+), 271 (M+2), 240 (M=-Et), 197 (M+–NEt₂), 154 (M+–NCH₂CH₂NEt₂), 86 (base peak, M+–CH₂NEt₂) Anal. Calc'd for C₁₃H₂₀N₃—OCl: C, 57.88; H, 7.47; N, 15.58. Fd. C, 58.05; H, 7.56; N, 15.30.
The formula is:

3-Chloroprocainamide, free base (1b)

N-(2-diethylamino-ethyl)-4-amino-3-chlorobenzamide hydrochloride (1a). The free base (1b) 22.1 g (0.082 moles) was placed in a flask and acidified to pH 2 with 85 mL of 1N HCl. The homogenous light yellow solution was divided up equally in five pre-weighed 100 mL lyophilization vials and frozen to −80° C. and lyophilized at high vacuum for one week in a Virtis Freeze-Dryer. Each vial was confirmed to contain 5.0 g (±0.1 g) of amorphous lyophilized material that was determined to be deliquescent. The yield of the hydrochloride (1a) was 100%. 1H NMR (D₂O) d 7.87 (s, 1H, ArH), 7.66 (d, J=2.8 Hz, 1H, ArH), 7.47 (s, 1H, NH), 7.29 (d, J=2.8 Hz, 1H, ArH), 3.74–3.78 (t, J=2.0 Hz, 2H, CH₂NHCO), 3.42–3.25 (m, 6H, (CH₂)₃N), 1.33–1.28 (t, J=2.4 Hz, 6H, N(CH₂CH₃)₂) IR (KBr) cm⁻¹, 3450, 3230 (NH₂, m), 1630, (C=O, s). Anal. Calc'd for C₁₃H₂₀N₃OCl—.HCl.2H₂O): C, 45.95; H, 6.47; N, 12.26. Fd. C, 45.62; H, 6.90; N, 12.28.

| Comp. | Mol. Weight | Amount (g) | Amount (mmol) | Remarks |
|---|---|---|---|---|
| (1) | 122.1 | 0.67 | 5.5 | Nicotinic Acid |
| (2) | 116.2 | 0.66 | 5.7 | p = 0.827 |
| EDC | 191.7 | 1.10 | 5.7 | 1-Ethyl-3-(3-di-methylaminopropyl) carbodidimido hydrochloride (Σ E-7750) |
| (3) | 220.28 | 1.1 | 5.0 | ≈100% yield |

Compound (1) (0.67 g, 5.5 mmol) and EDC (1.1 g, 5. 7 mmol) was dissolved in dimethyl sulfoxide (DMSO) (10 mL). N,N-dimethyl 1,2-ethylenediamine [compound (2)] (7.5 mL, 5.7 mmol) was added and the mixture was stirred at room temperature for 5 hours, whereafter the reaction mixture was freeze dried. The residue was subjected to column chromatography [silicon dioxide ($SiO_2$) plates chromatographed in chloroform ($CHCl_3$)-methanol (30:1, v/v)+triethylamine ($Et_3N$) (1:1, v/v). This procedure gave quantitative yield (1.1 g) of compound (3) as a syrup.

Elemental analysis for the free base form of N-(2-diethylamino-ethyl)nicotinamide. $C_{12}H_{19}N_3O$: Calculated; % C=65.12; H=8.65; N=18.99; O=7.23, Found; % C=65.2; H=8.6; N=19.0; O=7.2.

Figure 1:
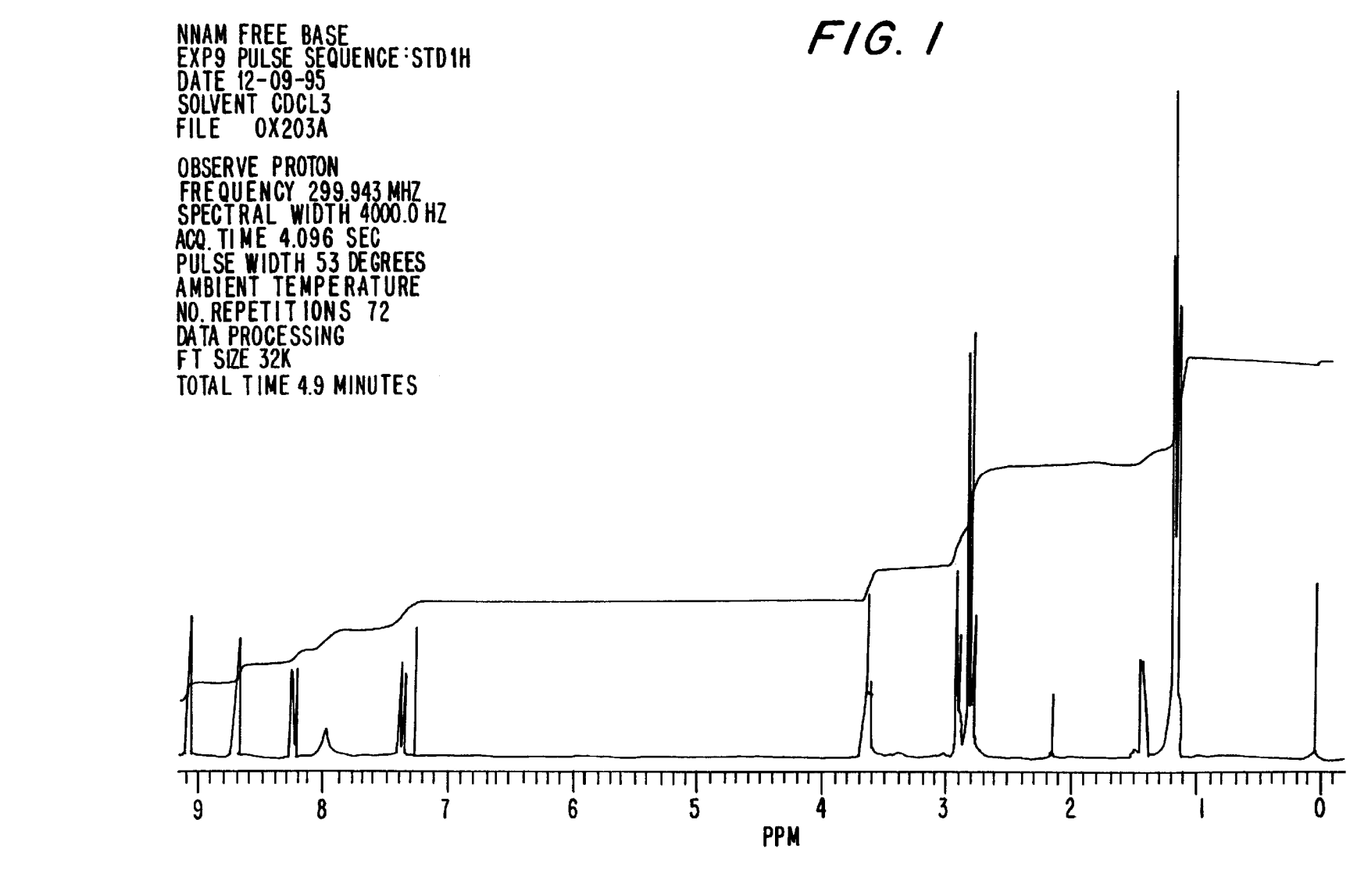
FIG. 1 is an NMR graph for the free base of N-(2-diethylamino-ethyl)nicotinamide in $CDCl_3$.

NMR assignments for the free base form of N-(2-diethylamino-ethyl)nicotinamide in $CDCl_3$ (FIG. 1). $^1$H-NMR data ($CH_2Cl_2$) gamma 9.10, 8.70, 8.22 and 7.3.9 (d, dd, dd, dd, 1H each, H-2 -6 -4 -5 in aromatic unit); 8.0 (bs, H, N—H); 3.63 (q, 2 H, $NCH_2C$); 2.92 (t, 2H, $NCCH_2NC_2$); 2.82 (q, 4H, 4×$NCH_2C$); 1.2(t, 6H, 2×$CH_3$). Solvent signal art 7.26 ($CHCl_3$).

Preparation of the hydrochloride salt of N-(2-diethylamino-ethyl)nicotinamide. The free base [compound (3)] was dissolved in n-propanol+n-butanol+0.1 M $HCl_{aq}$ (2:1:1, v/v/v). An aliquote of 2 M aqueous hydrochlorous acid was added to adjust the pH to 2. The solution was concentrated and the resulting amorphous material was dried under vacuum overnight. This material was readily soluble in water.

Figure 2:
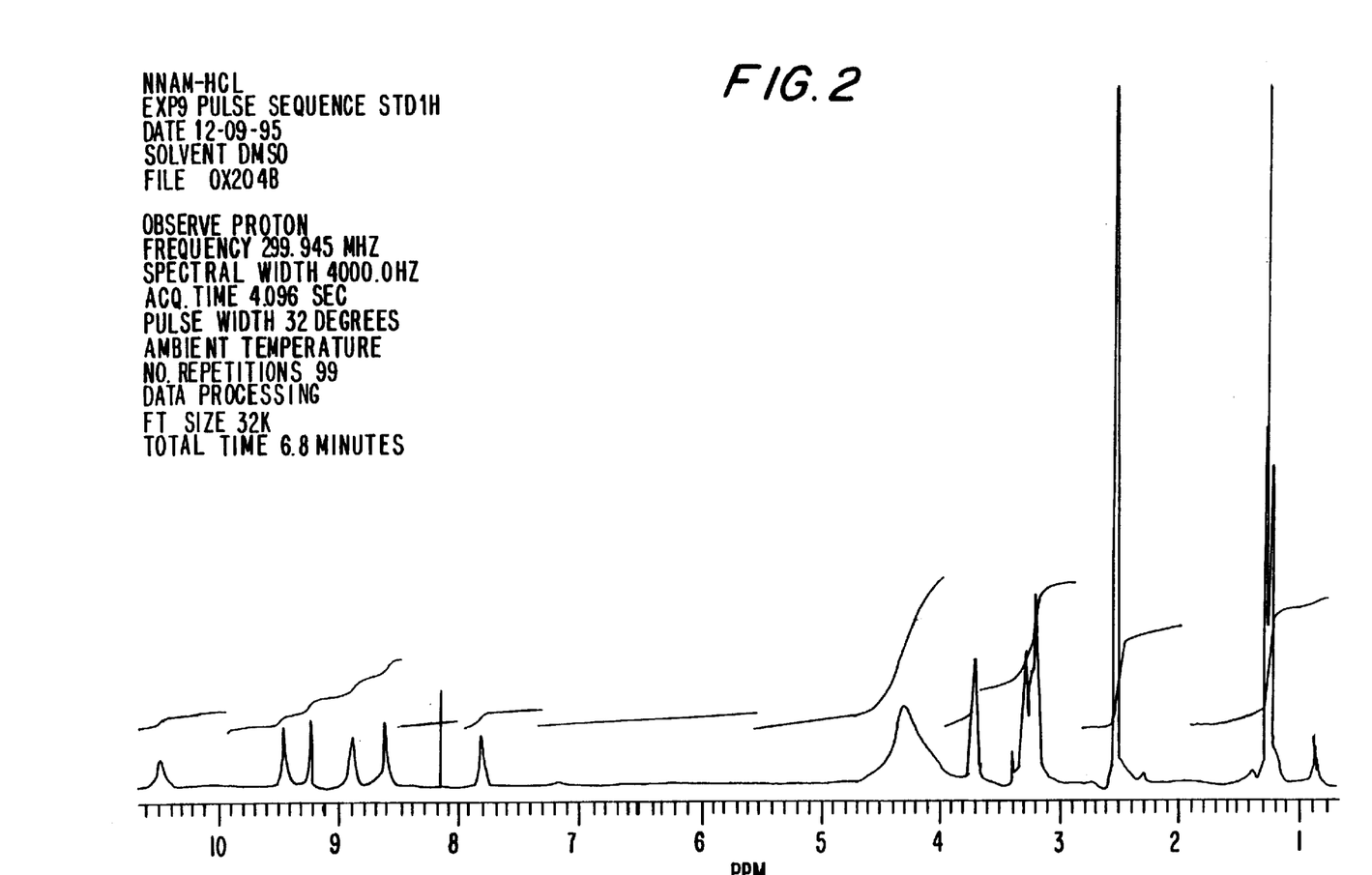
FIG. 2 is an NMR graph for the hydrochloride salt of N-(2-diethylamino-ethyl)nicotinamide in DMSO.
Figure 3:
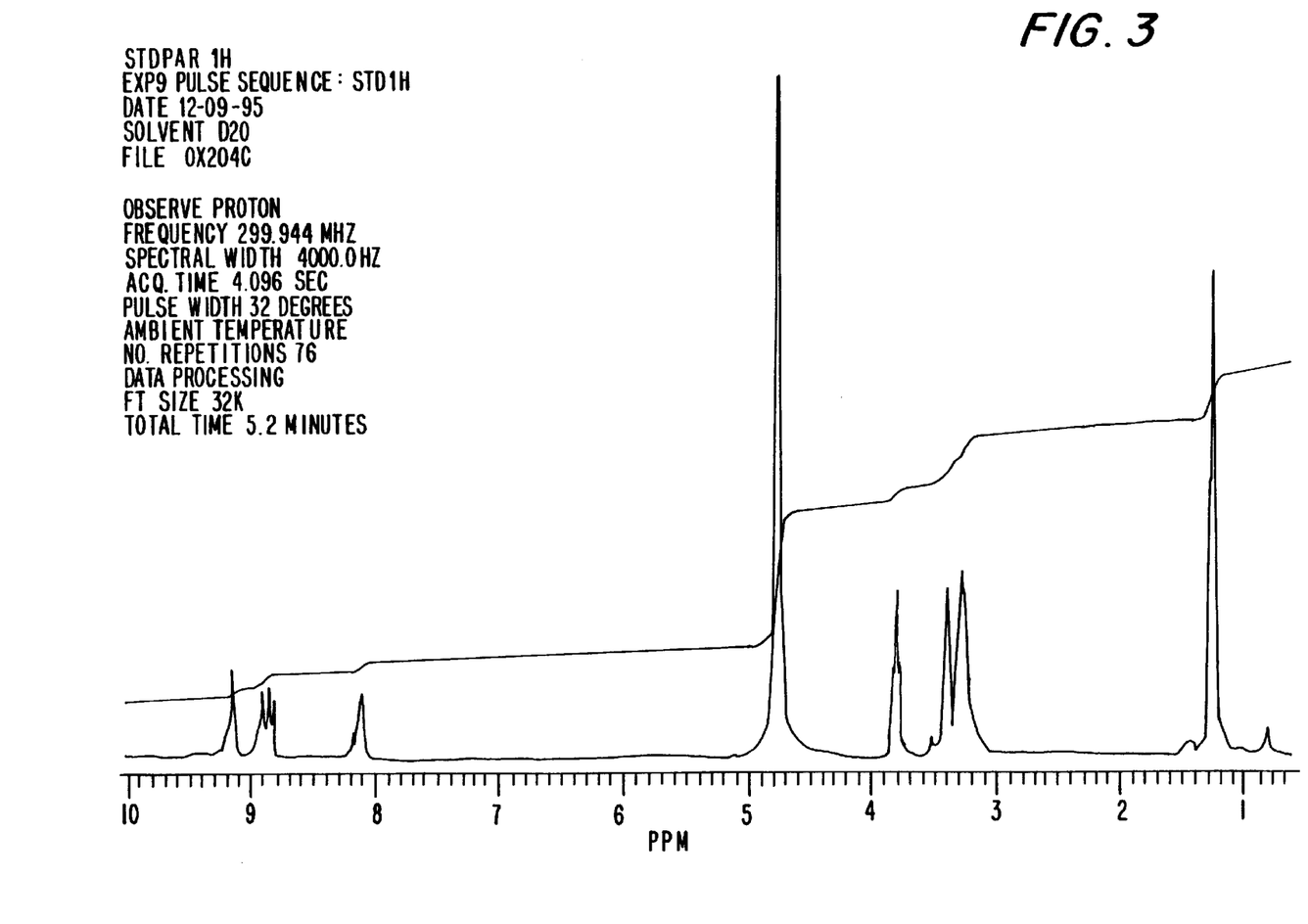
FIG. 3 is an NMR graph for the hydrochloride salt of N-(2-diethylamino-ethyl)nicotinamide in $D_2O$.

NMR assignments for the hydrochloride salt of N-(2-diethylamino-ethyl)nicotinamide in DMSO (FIG. 2) and $D_2O$ (FIG. 3). $^1$H-NMR data (DMSO-d6) gamma 10.5 (bs, 1 H, $HNC_3$); 9.46, 9.26, 8.90, 8.62, 7.82 (bt, bs, m, d, bt, 1×NH, 4×Ar-H); 3.7; (q, 2 H, $NCH_2C$); 3.3–3.1 (m, 6H, $H_2CN(CH_2C)_2$; 1.2 (t, 6H, 2×$CH_3$). The signals at 10.5 and 9.46 vanished on treatment with $D_2O$ (FIG. 3, H-D exchange). Solvent signal at 2.50 (DMSO-H).

The following procedures were then performed with the materials obtained as described above:

Reaction of aryl carboxamides with radiation. Aqueous 100 μM solutions of procainamide (4-amino-N-(2-diethylamino-ethyl)benzamide), 3-chloro-procainamide (N-(2-diethylamino-ethyl)-4-amino-3-chlorobenzamide), metoclopramide (4-amino-5-chloro-N-(2-diethylamino-ethyl)-2-methoxybenzamide), nicotinamide and N-(2-diethylamino-ethyl nicotinamide were given 1000 Gy of irradiation from $^{137}$cesium source (1.3 Gy/min., Scanditronix) at room temperature for 30 min. The various reaction mixtures were then vacuum evaporated to dryness, redissolved in methanol, spotted on silica gel 60 F245 thin layer chromatography (TLC) plates in 1-butanol:acetic acid:water (4:1:1, v/v/v), and visualized with short and long wave ultraviolet light and also in an iodine chamber, and the Rf values calculated in the conventional manner.

Evaluation of antitumor activity. 6–8 week old scid mice of both sexes were used. The average body weights were 19±1 gm for female and 22±3 gm for male mice. The animals were maintained under sterile but not specific pathogen-free conditions. The tumor line used H2981 that originated from a human lung adenocarcinoma and has been established in in vitro cell culture (Schreiber et al., Cancer Res. 52: 3252–66, 1992) and implanted into scid mice. The tumor grants were serially translated by subcutaneous inoculation of tumor cell suspension into the right flank of the mice. Neutralized metoclopramide (Neu-Sensamide™, Oxigene, Inc., New York, N.Y.) was provided as a 100 mg/ml (free base) sterile injectable concentration, pH 6.7–6.9. The chemical was diluted with sterile saline and was sterilized again by filtration (0.22 μM) at concentrations of 0.5 and 2.5 mg/ml. 100 μl of the drug was injected intramuscularly (i.m.) 2 h before irradiation, at final doses of 2 or 10 mg/kg body weight 3 times per week (Mondays, Tuesdays and Fridays) until the animals were sacrificed (i.e. when tumors were 15×15 mm, usually about 20 days). Control animals were injected with an equal volume of sterile saline as a placebo control. The animals were randomly divided into treatment groups, where no significant difference of sex, body weight or initial tumor volume between the groups was observed. At the first day of treatment the tumor volumes ranged from 30–95 $mm^3$. The tumor volumes were calculated as volume=$(L \times W^2)/2$ where L is the length and W is the width of the tumor.

Evaluation of radiosensitization by apoptotic cytotoxicity. Apoptosis or programmed cell death was evaluated in purified mononuclear leukocytes after 24 h exposure to 1 Gy radiation±0–10 mM doses of procainamide, 3-chloro-procainamide, metoclopramide, nicotinamide or N-(2-diethylamino-ethyl) nicotinamide. The cells were first exposed to the drugs for 30 minutes at 37° C. before being given 1 Gy irradiation ($^{137}$cesium source, Scanditronix, 1.56 Gy/min). The apoptotic and necrotic cells were analyzed and scored by phase contrast morphological criteria. Apoptotic cells have condensed chromatin and are trypan blue negative whereas necrotic cells stain blue with trypan blue. The morphological examination determining apoptotic cells was confirmed by measurements of apoptotic cells by flow cytometry and DNA frequency histograms stained with propidium iodide and incubated for 1 h before subjected to cytometric analysis.

EXAMPLES OF DATA

Example 1

Figure 4:
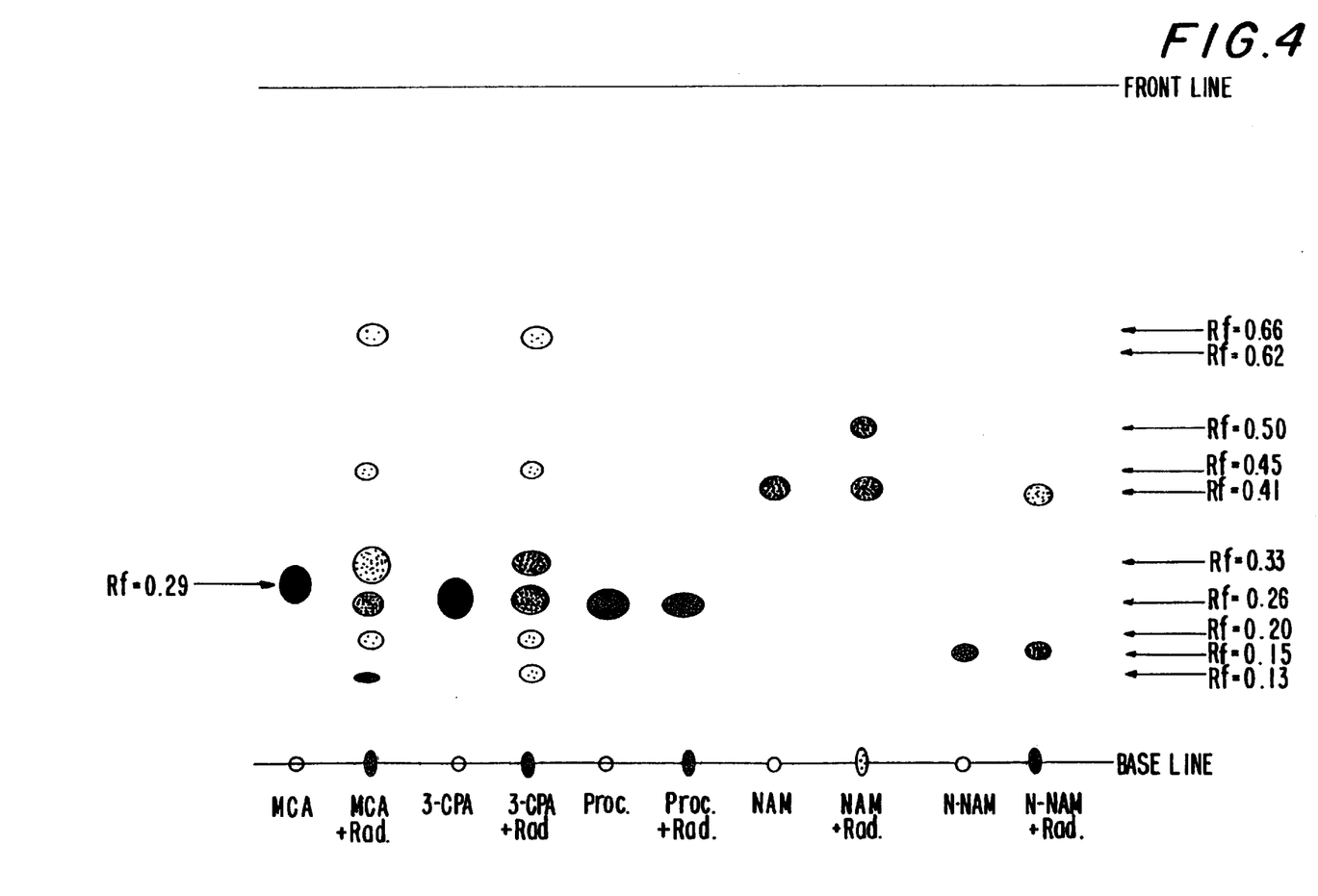
FIG. 4 is a thin layer chromatographic tracing of metoclopramide (MCA), procainamide (proc.), 3-choroprocainamide (3-CPA), nicotinamide (NAM) and N-(2-diethylamino-ethyl) nicotinamide (N-NAM) and in combination with gamma radiation (rad.)

Data for this Example are set forth in FIG. 4.

This example, together with Examples 2 and 3, shows that aryl N-substituted carboxamides, such as are represented by N-substituted benzamide and nicotinamide analogs, if they have the chemical property of being able to interact with a therapeutic agent (in this case radiation), then they can also manifest the biological property of enhancing, or either indirectly or directly, inducing cytotoxicity of importance for the control of tumor growth. For example, metoclopramide and 3-chloro-procainamide readily react with radiation producing at least 7 distinctive products identifiable by thin layer chromatography, whereas procainamide (a very similar chemical analog differing from these 2 drugs only by the lack of an aromatic chloride) does not react at all (FIG. 4). These data are exactly paralleled by their abilities to radiosensitize cytotoxicity where metoclopramide and 3-chloro-procainamide are effective but not procainamide (examples 2–3). Moreover, the identification of other important chemical features were obtained from biological and chemical structural analyses of the nicotinamide analogs. N-(2-diethylamino-ethyl)nicotinamide readily reacts with radiation (evidenced by intense spot at baseline and Rf=0.41) and also radiosensitizes cytotoxicity by apoptosis, but nicotinamide does not sensitize cytotoxicity by apoptosis and the reaction with radiation although present is much reduced (evidenced by weak spot at baseline and intense spot co-chromatographing with intact nicotinamide) compared to the N-substituted nicotinamide (FIG. 4). These data establish that aryl carboxamides must have the common chemical features of having an aryl N-substitution plus either aromatic nitrogen or aromatic halo substitutions before the interaction with a DNA damaging therapeutic agent becomes enhanced, and either a direct or indirect sensitization of cytotoxicity is apparent.

Example 2

Data for this Example are set forth in FIG. 5.

This Example demonstrates that when repeated doses of aryl N-substituted carboxamides such as Neu-Sensamide™ (a conformationally altered formulation of 4-amino-5-chloro-N-(2-diethylamino-ethyl)-2-methoxybenzamide or metoclopramide) are increased from lower doses such as 2 mg/kg to higher doses such as 10 mg/kg then there is a cytotoxic effect against tumors directly without the necessity of co-administration of radiation or chemotherapeutic drugs in order to enhance the cytotoxicity (FIG. 5). Hence, these data teach that aryl N-substituted carboxamides have potential anticancer value because they possess inherent antitumor effects by themselves.

Example 3

Figure 6A:
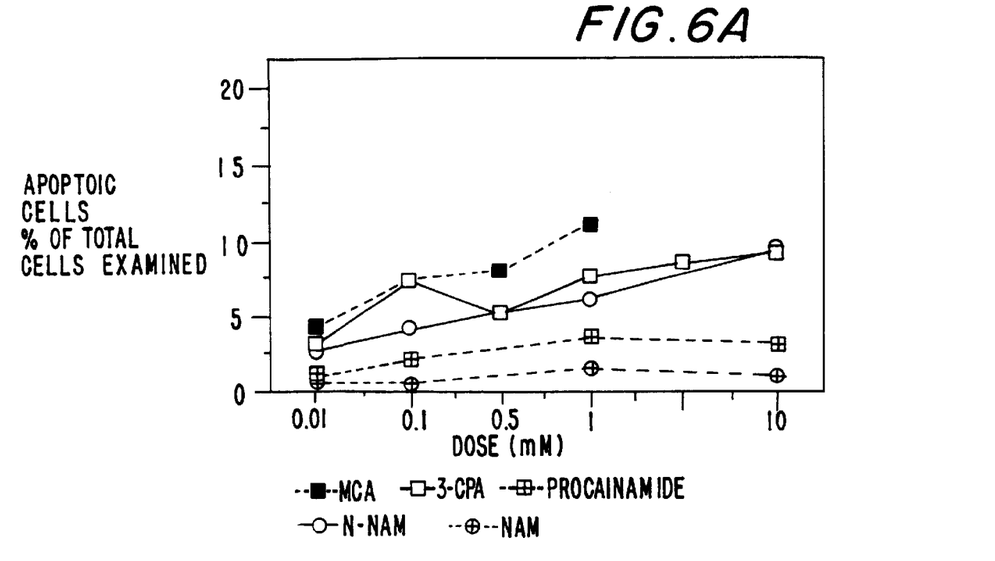
FIGS. 6A and 6B are graphs illustrating induction of apoptosis and necrosis in human lymphocytes at 48 hours after treatment with (FIG. 6A) NeuSensamide™ (MCA), 3-chloro-procainamide (3-CPA), procainamide, N-(2-diethylamino-ethyl)nicotinamide (N-NAM) and nicotinamide (NAM) or (FIG. 6B) ionizing radiation (1 Gy) in combination with 100 μM MCA or 1000 μM 3-CPA, procainamide, N-NAM and NAM.
Figure 6B:
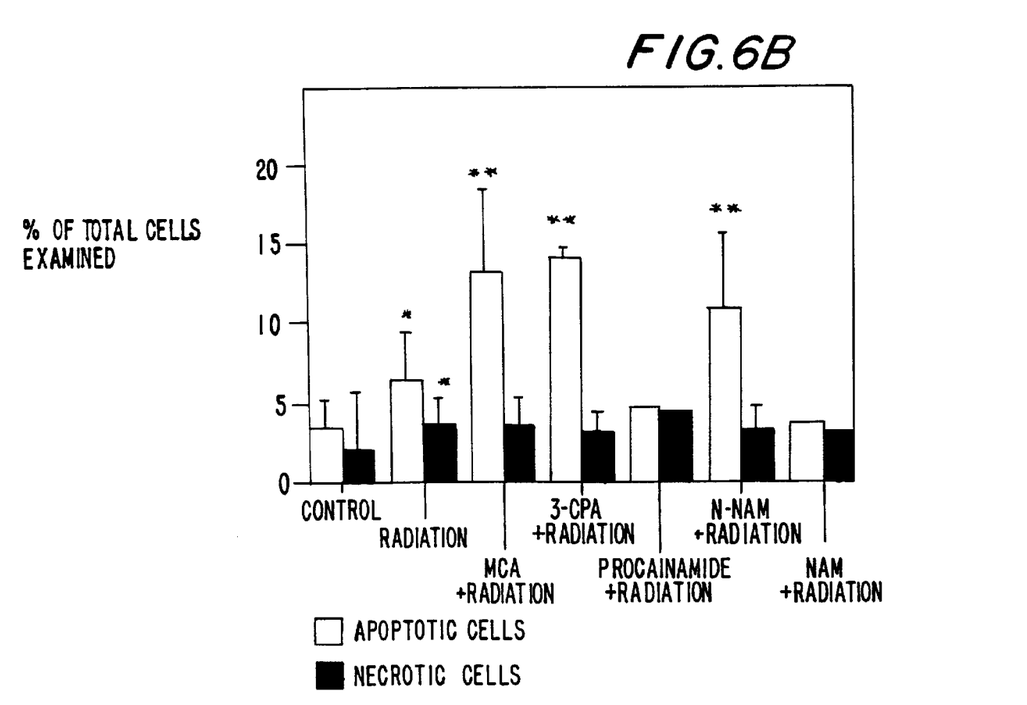

Data for this Example are set forth in FIGS. 6A and 6B.

This Example discloses two important observations. Firstly, aryl N-substituted carboxamides must have other chemical structural features in addition to the N-substitution before these agents can either induce cytotoxicity directly (FIG. 6A; see also Example 2) or sensitize radiation-induced cytotoxicity (FIG. 6B). These chemical features included the presence of an aryl halo substitution (e.g. 3-chloro-procainamide, metoclopramide) or an aromatic nitrogen (e.g. N-(2-diethylamino-ethyl) nicotinamide). Agents not including an aryl N-substituted carboxamide plus at least one other structural feature outlined above such as was the case with the examples procainamide (e.g. 4-amino-N-2-(diethylamino-ethyl) benzamide) and nicotinamide were not able to affect cytotoxicity by apoptosis. Second, this Example has shown along with example 2 that aryl N-substituted carboxamides containing aryl halo substitutions or an aromatic nitrogen were capable of inducing apoptotic cytotoxicity but not agents lacking these essential chemical features. Furthermore, these data show that the N-substituted benzamides and nicotinamides can induce effects on apoptotic cytotoxicity even when there are no measurable effects on killing cells by necrosis (i.e. reproductive/proliferative cell death). Because apoptosis is a normal physiological mechanism contributing to the pathological development of many human disorders including cancer, HIV/AIDS, psoriasis, Alzheimer's disease, Hodgkin's disease, Huntington's chorea, ischemic injury and many other autoimmune or neurodegenerative diseases (C. B. Thompson, Science 267:1456–62, 1995), this Example also indicates that the N-substituted aryl carboxamides such as benzamide and nicotinamide analogs are potentially useful therapeutic agents for the treatment of a wide variety of human diseases.

It is to be understood that the invention is not limited to the features and embodiments hereinabove specifically set forth, but may be carried out in other ways without departure from its spirit.

What is claimed is:

1. A method of inhibiting or killing tumor or cancer cells in a human patient, consisting essentially of treating the patient with a composition selected from the group consisting of N-(2-diethylamino-ethyl)-4-amino-3-chlorobenzamide, acid addition salts thereof, and mixtures thereof.

2. A method of inhibiting or killing tumor or cancer cells in a human patient, consisting essentially of treating the patient with radiation or a chemotherapeutic agent having a cytotoxic effect on said cells together with a composition selected from the group consisting of N-(2-diethylamino-ethyl)-4-amino-3-chlorobenzamide, acid addition salts thereof, and mixtures thereof, in an amount effective to enhance the cytotoxic effect of the radiation or chemotherapeutic agent employed.

3. A method of inhibiting or killing tumor or cancer cells in a human patient which comprises treating the patient with a composition comprising at least one compound selected from the group consisting of N-(2-diethylamino-ethyl)-4-amino-3-chlorobenzamide and acid addition salts thereof.

* * * * *